United States Patent
Chadwick et al.

(10) Patent No.: US 6,506,557 B2
(45) Date of Patent: Jan. 14, 2003

(54) METHODS AND COMPOSITIONS FOR IDENTIFYING A PROTEASE

(75) Inventors: Mark P. Chadwick, Cambridge (GB); Stephen J. Russell, Rochester, MN (US)

(73) Assignee: BioFocus Discovery Limited, Cambridge (GB)

(*) Notice: Subject to any disclaimer, the term of this patent is extended or adjusted under 35 U.S.C. 154(b) by 0 days.

(21) Appl. No.: 09/792,416

(22) Filed: Feb. 23, 2001

(65) Prior Publication Data

US 2002/0039729 A1 Apr. 4, 2002

Related U.S. Application Data

(60) Provisional application No. 60/184,981, filed on Feb. 25, 2000.

(51) Int. Cl.[7] .............. C12Q 1/70; C12Q 1/06; C01N 33/53; C12N 5/00; C12N 5/06
(52) U.S. Cl. .............. 435/5; 435/7.1; 435/39; 435/325; 435/334; 435/339
(58) Field of Search .............. 435/5, 7.1, 39, 435/325, 334, 339

(56) References Cited

U.S. PATENT DOCUMENTS

| | | | |
|---|---|---|---|
| 5,643,770 A | 7/1997 | Mason et al. | 435/172.3 |
| 5,723,287 A | 3/1998 | Russell et al. | 435/5 |
| 6,015,686 A | 1/2000 | Dubensky, Jr. et al. | 435/69.1 |

Primary Examiner—Hankyel T. Park
(74) Attorney, Agent, or Firm—Palmer & Dodge LLP; Kathleen M. Williams

(57) ABSTRACT

Methods are disclosed whereby protease activity is directly linked to replication of viral display packages containing protease-encoding polynucleotides in target cells. The methods can be used, inter alia, to identify proteases, including previously undiscovered proteases or variants of known proteases which may have altered substrate specificity.

60 Claims, 1 Drawing Sheet

PROTEASE CLONING BY MOLECULAR EVOLUTION.

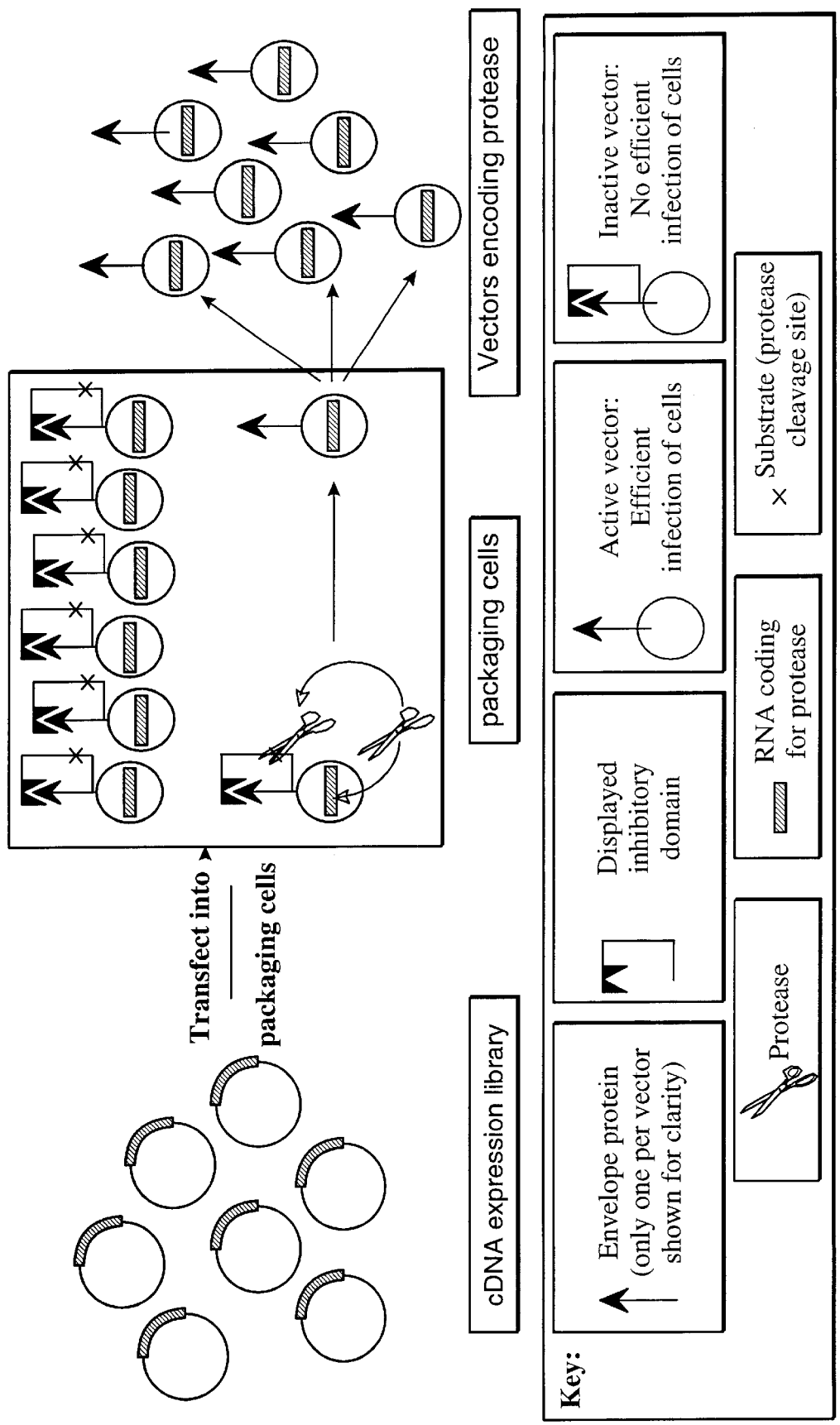

METHODS AND COMPOSITIONS FOR IDENTIFYING A PROTEASE

This application claims benefit of Provisional Application Ser. No. 60/184,981 filed Feb. 25, 2000.

TECHNICAL FIELD OF THE INVENTION

The invention relates to the identification and cloning of polynucleotides encoding proteases.

BACKGROUND OF THE INVENTION

Proteases are involved in a variety of cellular processes, such as tumor invasion, wound healing, tissue remodeling, infection, and inflammation. Previously unknown proteases whose substrate specificities are known can be used, for example, to design compounds which can affect these processes, including therapeutic compounds for conditions such as cancer, inflammation, rheumatoid arthritis and other autoimmune diseases, and AIDS.

Many methods are available in the art for detecting protease activity. For example, WO 97/08194 allegedly discloses a method of assaying for protease activity by measuring the fluorescence intensity of a fluorescent substrate. It would be advantageous to have a method in which detection of protease activity is linked to identification of a polynucleotide encoding the protease. Thus, there is a need in the art for convenient and rapid methods which can be used both for detection of protease activity and for identification of polynucleotides encoding the protease.

SUMMARY OF THE INVENTION

It is an object of the present invention to provide methods for identifying coding sequences for proteases which are expressed under a variety of conditions, including proteases which were previously unknown. This and other objects of the invention are provided by one or more of the embodiments described below.

One embodiment of the invention provides a method of identifying a candidate polynucleotide molecule encoding a protease. A first plurality of target cells which contain candidate polynucleotides is incubated under conditions which permit packaging of RNA corresponding to the candidate polynucleotides into viral display packages. The candidate polynucleotides may or may not encode a protease. The viral display packages display chimeric envelope proteins which comprise (I) a substantially intact viral envelope protein which enhances fusion between a viral membrane and a target cell membrane, (ii) an inhibitory protein which prevents fusion between the substantially intact viral envelope protein and a target cell membrane, and (iii) a protease recognition site located between the substantially intact viral envelope protein and the inhibitory protein. In another embodiment, the viral display packages display recombinant envelope proteins, in which a protease recognition site has been substituted for a furin cleavage site located between a large glycoprotein subunit of the envelope protein and a transmembrane component of the envelope protein. Recombinant envelope proteins can be derived from viral envelope proteins such as a Moloney murine leukemia virus envelope protein, a 4070A envelope protein, or an influenza virus envelope protein.

A "protease recognition site" according to the invention is a contiguous sequence of amino acids connected by peptide bonds which are recognized by a protease. Recognition of this site by a protease results in cleavage (i.e., hydrolysis) of peptide bond by the protease. The site of hydrolysis may be coincident with the protease recognition site, that is, the protease recognition site may include one or more amino acids on either side of the peptide bond to be hydrolyzed which are recognized by the particular protease. The specific sequence of amino acids in the protease recognition site depends on the catalytic mechanism of the protease, which is defined by the nature of the functional group at the protease's active site. Alternatively, the protease recognition site may be one, two, three, four or more amino acids distal at the amino or carboxy terminus, to the site of cleavage by the protease.

The viral display packages produced by the first plurality of target cells are contacted with a second plurality of target cells. Infection of a member of the second plurality of target cells by a viral display package occurs only if a protease produced in a member of the first plurality of target cells removes the inhibitory protein from the chimeric envelope protein or, if a recombinant envelope protein is displayed, only if a protease produced in a member of the first plurality of target cells cleaves at the protease recognition site between the large glycoprotein subunit and the transmembrane component of the recombinant envelope protein to activate the envelope protein's fusion activity. In a preferred embodiment, at least a third plurality of target cells is infected with a viral display package. If desired, the viral display package comprises a transferable label. The first, second, and at least third pluralities of target cells can be present in the same tissue culture vessel or in different tissue culture vessels.

Target cells can comprise a retroviral packaging signal, a viral long terminal repeat, and polynucleotides which encode packaging defective Gag, Pol polypeptides and a chimeric envelope protein. If desired, the retroviral packaging signal, the viral long terminal repeat, and the polynucleotides which encode Gag and Pol polypeptides and the chimeric envelope protein can be encoded in the same polynucleotide molecule as a candidate polynucleotide. If desired, members of the first and second pluralities of target cells can be the same cell type, such as a retroviral packaging cell line.

Target cells may be treated with growth factors, activating proteases or other protease-modulating compounds to modulate the protease activity of the target cells.

As used herein, the term "treatment to modulate protease activity" refers to a process or treatment that results in activation of a protease expressed in a zymogen or proenzyme form. This treatment may, for example, activate or even introduce a proteolytic enzyme required for cleavage of a zymogen form of a protease.

As used herein, the term "growth factor" refers to a polypeptide that alters protease activity in a cell through interaction of the polypeptide with a specific receptor expressed by that cell.

As used herein, the term "activating protease" refers to a proteolytic activity that, through cleavage of one or more polypeptides, modulates the activity of a cellular protease.

As used herein, the term "protease-modulating compound" refers to a compound that directly or indirectly activates a cellular protease.

In preferred embodiments, the chimeric envelope protein comprises a substantially intact retroviral envelope protein, preferably a murine leukemia virus envelope protein, such as a 4070A or Moloney murine leukemia virus envelope protein.

In one embodiment, the inhibitory protein binds to a receptor present on the outer cell membrane of the target cell. The inhibitory protein can be, for example, CD3 antigen, epidermal growth factor, stem cell factor, and an insulin-like growth factor I.

In another embodiment, a first inhibitory protein oligomerizes with at least second inhibitory protein, such as CD40 ligand or a leucine zipper polypeptide, for example GCN4, C/EBP, Fos, Jun, and c-myc.

Candidate polynucleotides can be obtained from a cell which is not known to express a protease, from a cell which is known to express a protease, or from a cell which is likely to express a protease, such as a tumor cell, a cell of a tissue which is inflamed, a cell of a tissue which is undergoing remodeling, a cell of a tissue which is involved in wound healing, or a cell comprising an infectious agent which expresses a protease. Optionally, candidate polynucleotides are synthetic polynucleotides.

Sequences which permit integration of candidate polynucleotides into the genome of a target cell, such as retroviral long terminal repeats, can be included in candidate polynucleotide molecules. Endoplasmic reticulum or Golgi retention/retrieval signals also can be included in candidate polynucleotide molecules.

Preferably, primers are included in the candidate polynucleotide molecules, for use in amplifying a candidate polynucleotide molecule which encodes a protease. Amplified candidate polynucleotide molecules can then be sequenced.

The protease recognition site can be a variation of a cleavage site of a known protease. Preferably, the variation of the known cleavage site is formed by modifying at least one amino acid of the known protease recognition site.

Thus, the present invention provides an innovative approach to the identification of protease coding sequences.

BRIEF DESCRIPTION OF THE DRAWINGS

FIG. 1 is a schematic view of a method of cloning an unknown protease. The cDNA expression library is transfected into the packaging cells. The corresponding RNA is then packaged into inactive retroviral particles. The particles are inactive because they display an inhibitory domain. Some of the cDNA's will code for proteases which can remove the inhibitory domain, thus activating the vector. Only those proteases which cleave the specific substrate sequence in the vector construct will activate the vectors. The activated vectors will then infect other cells, thus spreading the protease cDNA sequence throughout the cell population.

DETAILED DESCRIPTION

It is a discovery of the present invention that the components described below can be assembled to provide a system in which a polynucleotide molecule encoding a protease is selectively replicated by means of its inclusion in a viral display package capable of infecting one or more successive generations of target cells. Candidate polynucleotides which may or may not encode a protease are packaged into viral display packages by members of a first plurality of target cells which contain the candidate polynucleotides. The viral display packages comprise a chimeric envelope protein, which is displayed on the surface of the viral display packages. In one embodiment, the chimeric envelope protein comprises 3 components, from N- to C-terminus: (I) an inhibitory protein which prevents fusion between the substantially intact viral envelope protein and a target cell membrane, (ii) a protease recognition site located between the substantially intact viral envelope protein and the inhibitory protein, and (iii) a substantially intact viral envelope protein which enhances fusion between a viral membrane and a target cell membrane. The presence of the inhibitor protein in the chimeric envelope protein prevents fusion of the substantially intact viral envelope protein and the target cell membrane. In another embodiment, the viral display packages display recombinant envelope proteins, in which a protease recognition site has been substituted for a furin cleavage site located between a large glycoprotein subunit of the envelope protein and a transmembrane component of the envelope protein (such as between SU and TM in murine leukaemia viruses or between HA1 and HA2 in influenza virus). In this case, cleavage of the site activates the envelope protein, such that the transmembrane component can mediate fusion with the target cell line.

Viral display packages formed in members of the first plurality of target cells may or may not contain RNA corresponding to a protease-encoding candidate polynucleotide. If viral display packages are formed in a target cell which expresses a protease which can hydrolyze a peptide bond in the protease recognition site, the inhibitory protein will be removed from the chimeric envelope protein of those viral display packages. Those viral display packages will then be activated, i.e., capable of infecting a target cell by fusing with and transferring their contents to a target cell via the substantially intact viral envelope protein. Because the viral display packages will have packaged RNA molecules corresponding to the protease-encoding candidate polynucleotide, this RNA will be transferred to the infected target cells. Thus, infection of target cells occurs only if a protease produced in the first plurality of target cells removes the inhibitory protein from the chimeric envelope protein. "Occurrence of target cell infection" according to the invention includes an increased level of infection, for example, at least 10%, 20%, 30%, 40%, or 50% more infection of target cells in the presence of a protease than in the absence of the protease.

The cycle of infection is repeated at least 1, preferably 2, 3, 4, or 5 more times. A proportion of the culture medium (containing viral display packages), e.g., 10, 20, 25, 30, or 40%, is then transferred to uninfected target cells. Additional cycles of infection can then occur. This cycle can be repeated 2, 3, 4, 5, 6, 7, 8, 9, or 10 or 20 or more times, until ultimately most of the target cells in a culture vessel contain the protease-encoding candidate polynucleotide. In addition, the candidate polynucleotides may also contain an antibiotic resistance gene, such as a neomycin, phleomycin, or puromycin resistance gene, to aid selection of infected cells.

An alternative method of identifying a protease is to carry out the method described above using viral display packages which display a recombinant envelope protein, rather than a chimeric envelope protein. Envelope proteins comprise a large glycoprotein subunit (e.g. SU in Moloney murine leukemia virus or HA1 in influenza virus) and a smaller transmembrane subunit (e.g. TM in Moloney murine leukemia virus or HA2 in influenza virus). The two components are separated by a furin cleavage site. The large glycoprotein subunit mediates attachment to a cellular receptor. The transmembrane component mediates fusion between the viral and cellular membranes when furin cleavage activates the envelope protein.

Recombinant envelope proteins of the invention are envelope proteins in which a protease recognition site according to the invention has been substituted for the furin cleavage site. In this case, a viral display package displaying a recombinant envelope protein is activated when a protease hydrolyzes a peptide bond in the protease recognition site to enable the transmembrane component to mediate fusion with the target cell membrane.

This discovery permits the discovery of new proteases, whether they are previously undiscovered proteases or amino acid sequence variants of previously known proteases having altered substrate specificity, by identifying a polynucleotide molecule encoding a new protease. Thus, cloning of a protease-encoding polynucleotide according to the invention can be achieved when the cleavage site of the unknown protease is known. Once the polynucleotide is identified and cloned, the amino acid sequence of the encoded protease can be deduced and the protease identified. This method is particularly useful, for example, when it is discovered that an extracellular portion of a receptor is shed from the cell surface by the action of an unknown protease. In addition, proteases with altered or novel substrate specificities can be detected, using candidate polynucleotides which encode known proteases in which the active site has been altered and assaying the encoded proteases for the ability to cleave a protease recognition site which has also been altered. Such proteases can be used to degrade proteins which are overexpressed in diseases such as Alzheimer's disease or cancer, or for removing a pathogenic organism attached to a cell surface receptor, such as a receptor present on the respiratory lining. Identified proteases can also be used for agricultural purposes, for example to degrade essential proteins of a pest on a crop, particularly a commercial crop.

A particular advantage of the present invention is that protease-encoding polynucleotide molecules can be selected from a plurality of cells without the need for cell sorting. Another advantage is that the protease so identified is identified in a physiological environment and therefore is active in a physiological environment. The identified proteases can be used, for example, to screen for inhibitors of the protease which can be used therapeutically, for treating conditions such as cancer, rheumatoid arthritis or other autoimmune diseases, inflammation, or infections such as AIDS or herpes.

Proteases Identifiable According to the Invention

A "protease" which can be identified according to the invention is an enzyme which hydrolyzes a peptide bond between a pair of amino acids located in a polypeptide chain, also called an endoprotease. Proteases are typically defined by reference to the nucleophile in the catalytic center of the enzyme. The most common nucleophiles arise from the side chains of serine, aspartic acid, and cysteine, resulting in families of proteases, such as serine proteases (Paetzel et al., *Trends Biochem. Sci.* 22, 28–31, 1997), aspartyl proteases (Spinelli et al., *Biochemie* 73, 1391–96, 1991), and cysteine proteases (Altschuh et al., *Prot. Eng.* 7, 769–75, 1994). Metalloproteases usually contain a zinc catalytic metal ion at the catalytic site (Klimpel et al., 1994, *Mol. Microbiol.* 13, 1093–100). Examples of members of each of these protease families are provided in Table I.

TABLE I

Proteases and Protease Recognition Sites (* indicates the peptide bond being hydrolyzed)

| Protease Family | Protease | Protease Recognition Sites |
|---|---|---|
| serine | factor Xa | Ile—Gly—Gly—Arg* |
| serine | trypsin | Lys*, Arg* |
| serine | chymotrypsin | Tyr*, Phe*, Leu*, Ile*, Val*, Trp*, and His* at high pH |
| serine | thrombin | Arg* |
| serine and cysteine variants | peanut mottle polyvirus Nla protease | Glu—Xaa—Xaa—Tyr—Gln*(Ser/Gly) |
| cysteine | papain | Arg*, Lys*, Phe* |
| cysteine | bromelain | Lys*, Ala*, Tyr*, Gly* |
| cysteine | cathepsin B | Arg*Arg, Phe*Arg |
| cysteine | cathepsin L | Phe*Arg |
| aspartyl | HIV protease | Phe*Pro |
| aspartyl | *S. cerevisiae* yapsin 2 | Lys*, Arg* |
| aspartyl | cathepsin D | Phe*Phe, Phe*Lys, Leu*Phe, Leu*Tyr |
| metallo- | thermolysin | *Tyr, *Phe, *Leu, *Ile, *Val, *Trp, and *His |
| metallo- | peptidyl-Lys metalloendopeptidase | Xaa*Lys |
| metallo- | peptidyl-Asp metalloendopeptidase | Xaa*Asp, Xaa*Glu, Xaa*Cys |
| metallo- | coccolysin | *Leu, *Phe, *Tyr, *Ala |
| metallo- | autolysin | Leu—Trp—Met*Arg—Phe—Ala |
| metallo- | gelatinase A (MMP-2) | Pro—Gln—Gly*Ile—Ala—Gly—Gln |
| metallo | Human neutrophil collagenase (MMP-8) | Gly—Leu—Ser—Ser—Asn—Pro*—Iie—Gln—Pro |

Protease Recognition Sites

A "protease recognition site" according to the invention is a contiguous sequence of amino acids connected by peptide bonds which contains a pair of amino acids which is connected by a peptide bond that is hydrolyzed by a particular protease. Optionally, a protease recognition site according to the invention may include one or more amino acids on either side of the peptide bond to be hydrolyzed, to which the catalytic site of the protease also binds (Schecter and Berger, *Biochem. Biophys. Res. Commun.* 27, 157–62, 1967), or the recognition site and cleavage site on the protease substrate may be two different sites that are separated by one or more (e.g., two to four) amino acids. If the protease recognition and cleavage sites are distinct sites on the protease substrate, then the recognition sites is positioned between the substantially intact viral envelope protein and the inhibitory domain in the chimeric envelope protein, and the cleavage site is present on one or the other side of the recognition site such that cleavage removes the inhibitory domain to permit infection of the second plurality of target cells by the viral package. That is, cleavage should not interfere with the ability of the substantially intact viral envelope protein to enhance fusion with the target all membrane and proceed with infection.

The specific sequence of amino acids in the protease recognition site depends on the catalytic mechanism of the protease, which is defined by the nature of the functional group at the protease's active site, as discussed above. For example, trypsin hydrolyzes peptide bonds whose carbonyl function is donated by either a lysine or an arginine residue, regardless of the length or amino acid sequence of the polypeptide chain. Factor Xa, however, recognizes the specific sequence Ile-Glu-Gly-Arg and hydrolyzes peptide bonds on the C-terminal side of the Arg.

Thus, a protease recognition site comprises at least 2, 3, 4, 5, 6, 7, 8, 9, or 10 or more amino acids. Optionally, additional amino acids can be present at the N-terminus and/or C-terminus of the recognition site. A protease recognition site according to the invention also can be a variant of a recognition site of a known protease, such as the recognition sites shown in Table I, above.

Optionally, a protease recognition site can be selected using a method such as that taught in U.S. Pat. No. 5,780,279. This method involves producing a fusion gene encoding a polypeptide, a substrate peptide, and at least a portion of a phage coat protein. The DNA encoding the substrate peptide is mutated at one or more codons to generate a family of mutants. The mutant fusion proteins are expressed on the surface of a phagemid particle and then exposed to a protease which may or may not recognize and cleave the mutant substrate peptide. If cleavage does occur, the polypeptide will become dissociated from the phagemid particle, and when the phagemid particle is contacted with an affinity molecule specific for the polypeptide, it will not bind. Thus, phagemid particles which express mutant fusion proteins comprising a substrate peptide which can be cleaved by a protease can be separated from those which do not express such fusion proteins. The substrate peptide so identified can be used to provide a protease recognition site for use in methods of the invention.

Viral Display Packages

"Viral display packages" are well known in the art (see, e.g., U.S. Pat. No. 5,723,287). Viral display packages of the invention display either recombinant envelope proteins or chimeric envelope proteins on their surface. Production of viral display packages is taught, for example, in U.S. Pat. No. 5,723,287, and in Chadwick et al., 1999. Briefly, viral packaging cells, such as Psi 2, TELCeB.6, and PA317, are conveniently used to produce viral display packages. The packaging cells comprise either a nucleic acid molecule which encodes a chimeric envelope protein or a nucleic acid molecule which encodes a recombinant envelope protein.

Chimeric Envelope Proteins

A "chimeric envelope protein" has the following three components from N- to C-terminus: (1) an inhibitory protein, which is capable of impairing the function of the envelope protein and hence fusion of the envelope protein with its target cell membrane, (2) a protease recognition site, and (3) a substantially intact viral envelope protein which mediates fusion between the viral display package and the target cell membrane, i.e. enhances fusion above the level of fusion which occurs in the absence of the substantially intact viral envelope protein.

Nucleic acid molecules encoding chimeric envelope proteins can be produced using recombinant DNA technology or can be synthesized using standard nucleic acid synthesis techniques. Envelope proteins of adenovirus, togavirus, rhabdovirus, and retrovirus families, as well as from enveloped viruses such as paramyxovirus and orthomyxovirus, are useful in the chimeric envelope protein. Murine leukemia virus envelope proteins, such as the 4070A and Moloney MLV envelope proteins, are particularly useful for this purpose.

1. Viral Envelope Proteins

It is important that the viral envelope protein is substantially intact, i.e. retains all its domains, to conserve post-translational processing, oligomerization, viral incorporation, and fusogenic activities. However, certain alterations, such as mutations, deletions, or additions, can be made to the viral envelope protein which do not significantly affect these functions, and viral envelope proteins with such modifications are considered substantially intact. It is not necessary that an entire viral envelope protein be used, but the portion of the viral envelope protein included in the chimeric envelope protein must be able to mediate fusion between the viral display package and the outer cellular membrane of the target cell.

2. Inhibitory Proteins

An "inhibitory protein" useful in the chimeric envelope protein is a protein or a portion of a protein which prevents the substantially intact viral envelope protein from mediating fusion of the viral display package with the cell membrane of a target cell. At least two types of inhibitory proteins are useful in the chimeric envelope protein.

One type of inhibitory protein binds to a receptor on the target cell. This type of inhibitory protein thus may include, but is not limited to, a single-chain antibody fragment to a hapten (Russell et al., *Nucleic Acids Research* 21(5), 1081–1085, 1993), CD3 or colonic carcinoma cell antigens (Ager et al., *Human Gene Therapy* 7(17), 2157–2164, 1996), or a cellular growth factors such as epidermal growth factor (EGF, Cosset et al., *Journal of Virology* 69(10), 6314–6322, 1995), stem cell factor (SCF, Fielding et al., *Blood* 91(5), 1802–9, 1998), and insulin-like growth factor I (IGF-I, Chadwick et al., *J Mol Biol* 285(2), 485–94, 1999).

Amino acid sequences of such inhibitory proteins, as well as nucleotide sequences encoding them, are available in the scientific literature and in databases such as GenBank. For example, the nucleotide sequence encoding the 53 amino acids of EGF can be obtained from a cDNA template (ATCC 59957) using primers disclosed in Cosset et al. (1995). Primers for amplifying a cDNA sequence encoding SCF (e.g., GenBank Accession No. U80930.1) are disclosed in Fielding et al. (1998). Primers for amplifying IGF-I cDNA (GenBank Accession No. M37484) are disclosed in Chadwick et al. (1999). Alternate nucleotide sequences which encode these inhibitory proteins also can be synthesized and used to produce an inhibitory protein.

A receptor for an inhibitory protein can be present naturally on the target cell membrane or can be introduced into the target cell such that it is expressed as a heterologous receptor on the cell surface using standard molecular biological techniques. For example, the nucleotide sequence encoding the type-I IGF receptor is disclosed in Ullrich et al., *EMBO J.* 5(100), 2503–12 (1986) and in GenBank Accession No. X04434 M 24599. The nucleotide sequence encoding the EGF receptor is disclosed in Ullrich et al., *Nature* 309 (5967), 418–25 (1984) and in GenBank Accession No. X00588. Yarden et al., *EMBO J.* 6(11), 3341–51 (1987), and GenBank Accession No. X06182 disclose the coding sequence for the SCF receptor.

Another type of inhibitory protein oligomenzes with at least one, preferably two other inhibitory proteins of the same type in other chimeric envelope proteins. This type of inhibitory protein includes trimeric polypeptides such as the C-terminal extracellular domain of CD40 ligand (Karpusas et al., 1995, *Structure* 3, 1031–39), as well as leucine zipper polypeptides (Harbury et al., 1993, *Science* 262, 1401–07). Leucine zipper polypeptides according to the invention characteristically possess two domains—a leucine zipper structural domain and a basic domain that is rich in basic amino acids (Vinson et al., 1989, *Science,* 246, 911–916). The two domains are separated by a short segment known as the fork. Leucine zipper polypeptides include the yeast transcription factor GCN4, the mammalian transcription factor CCAAT/enhancer-binding protein C/EBP (Landschulz et al., *Science* 243, 1681, 1989), the nuclear transforming oncogene products Fos and Jun (O'Shea et al., *Science* 245, 646, 1989; Turner and Tjian, *Science* 243, 1689, 1989), and the gene product of the murine proto-oncogene, c-myc (Landschulz et al., *Science* 240, 1759, 1988). Preparation of 4070A and Moloney MLV envelope proteins comprising such inhibitory proteins is disclosed in Morling et al., *Virology* 234(1), 51–61, 1997.

An inhibitory protein may be a full-length protein or it may be that portion of the protein that either oligomerizes or binds to the corresponding receptor present on the target cell membrane. It is well known that amino acids of a protein which—binds to a receptor can be deleted without affecting the receptor-binding portion of the protein. For example, U.S. Pat. No. 5,859,208 discloses alterations which can be made to fibroblast growth factor without affecting its receptor binding domain. Similarly, U.S. Pat. No. 5,849,689 discloses alterations which can be made to hepatocyte growth factor. Leucine zipper polypeptides can also be modified without affecting their ability to oligomerize (see van Heeckeren et al., 1992, *Nucleic Acids Res.* 20, 3721–24). Portions of inhibitory proteins can be screened for the ability to prevent delivery of the contents of a viral display package using routine screening methods. For example, a portion of an inhibitory protein can be included in a chimeric envelope protein and tested for the ability to block gene transfer or transfer of a label, as described in Cosset et al., 1995 (*J. Virol.* 69, 6314–22).

Mechanism of Action

Without being bound to any particular mechanism of action, an inhibitory protein which binds to a receptor on the target cell is believed to prevent delivery of the contents of the viral display package to the target cell by receptor-mediated sequestration. Receptor-mediated sequestration occurs when receptors for an inhibitory protein are present on the surface of the target cell. Binding of the chimeric envelope protein to a cell surface receptor by means of the inhibitory protein of the chimeric envelope protein sequesters the viral display package and thus prevents it from binding a viral envelope protein receptor on the cell surface. Thus, the viral display package cannot bind to the viral receptor on the cell surface or fuse to the cell membrane and transfer a label (such as a gene).

Similarly, without being bound to any particular mechanism of action, it is believed that an inhibitory protein which oligomerizes impairs gene delivery by formation of an oligomeric cap on a viral glycoprotein (WO 90/04562; Morling et al., *Virology* 234(1), 51–61, 1997). The oligomeric cap forms by intermolecular association between inhibitory proteins displayed on different chimeric envelope proteins. The intermolecular association may be via non-covalent bonds or via covalent bonds, such as disulfide bonds. For example, the C-terminal extracellular domain of CD40 ligand forms such an oligomeric cap when displayed on a trimeric chimeric envelope protein. CD40 ligand is a homotrimer and therefore exhibits the same stoichiometry of association as the envelope glycoprotein itself. CD40 ligand displays significantly reduced envelope-protein mediated transfer to target cells by inhibiting binding of the envelope protein to its receptor and likely also by inhibiting subsequent fusion triggering, which requires the dissociation of a trimeric envelope protein into its subunits. Display of trimeric leucine zipper polypeptides produces a similar phenotype via the formation of an oligomeric cap (Morling et al., 1997).

Recombinant Envelope Proteins

A "recombinant envelope protein" of the invention is derived from any viral envelope protein which comprises a large glycoprotein subunit which is capable of binding to a cognate viral envelope receptor on the surface of the target cell, a furin cleavage site, and a transmembrane component which mediates fusion between the viral membrane and the membrane of the target cell.

In a recombinant envelope protein of the invention, a protease recognition site has been substituted for the furin cleavage site, at the same position in the envelope protein. Envelope proteins such as the envelope proteins of Moloney murine leukemia virus, 4070A virus, or influenza virus, can be used to derive a recombinant envelope protein. If a Moloney murine leukemia virus is used, the protease recognition site is located between the large glycoprotein subunit (SU) and the transmembrane component (TM). If an influenza virus envelope protein is used, the protease recognition site is located between the HA1 and HA2 portions of the envelope protein. Such recombinant envelope proteins can be constructed using standard molecular biology techniques, to delete the furin cleavage site of an envelope protein and substitute a desired protease recognition site.

Transferable Labels

A viral display package can also comprise a "transferable label" to facilitate identification and selection of target cells which have been infected by a viral display package. A transferable label can be any label whose presence can be detected in the target cell upon fusion of the viral display package and the target cell membrane. Preferably, the transferable label is a gene encoding a selectable marker or a reporter gene.

Genes encoding selectable markers are preferably antibiotic-resistance genes, such as a neomycin, puromycin, or phleomycin resistance gene. Reporter genes encode a detectable product, such as β-galactosidase, luciferase, β-glucuronidase, green fluorescent protein (GFP), autofluorescent proteins, including blue fluorescent protein (BFP), glutathione-S-transferase (GST), luciferase, horseradish peroxidase (HRP), or chloramphenicol acetyltransferase (CAT). Many such genes are known in the art. Transferable labels also include proteins which can be detected using immunochemical techniques employing antibodies which specifically bind to the protein product.

Polynucleotides encoding selectable markers or reporter gene products can be transfected into target cells as described above, for subsequent packaging into viral display packages. Alternatively, an antibiotic resistance gene or reporter gene can be included in a candidate polynucleotide, either up- or downstream from the open reading frame of the candidate polynucleotide.

Candidate Polynucleotides

A "candidate polynucleotide" according to the invention comprises a coding sequence for a protein, including a protease. The term "candidate polynucleotide" encompasses a single candidate polynucleotide molecule or a plurality of two or more of such molecules, ideally representing a plurality of (e.g., 5,000 to 10,000, 10,000 to 20,000, 20,000 to 30,000, 30,000 to 50,000, 50,000 to 100,000, or $10^6$ or $10^7$) of such polynucleotides to be screened according to the invention.

Candidate polynucleotides contain less than a whole chromosome and can be RNA or single- or double-stranded genomic or cDNA. Preferably the polynucleotides are isolated free of other cellular components, such as membrane components, proteins, and lipids. They can be made by a cell and isolated, or synthesized in the laboratory using an amplification method such as PCR or using an automatic synthesizer. Methods for purifying and isolating DNA are routine and are known in the art (for example, see Sambrook et al., Molecular Cloning, 2d ed., 1989; Perbal, A Practical Guide to Molecular Cloning, 2d ed., 1988).

Candidate polynucleotides can be obtained from cells not known to express a protease, cells which are likely to express a protease, such as cancer cells, or from cells which are known to express a protease. Cells which are likely to express proteases are obtained, for example, from tissues which are known to produce substantial proteolysis, such as a tumor, a tissue which is inflamed, a tissue which is undergoing remodeling, such as a developing limb bud, or a tissue which is involved in wound healing. Cells comprising a pathogen, such as an HIV virus, a rhinovirus, a herpes viruses, a hepatitis virus, or other infectious agent which express proteases, also can provide candidate polynucleotides. Cells which express a protease can be identified, for example, using protease assays employing substrates which produce a detectable product, such as a chromogenic or fluorescent substrate. Substrates and protease assay kits are commercially available from companies such as Molecular Probes, Inc., Promega, and CLONTECH.

Candidate polynucleotides can be present in plasmids of a cDNA expression library, which cDNA library can be constructed from cells known to express a protease. Ideally, the cDNA expression library will include a plurality of plasmids, where each plasmid contains an expression cassette comprising a candidate polynucleotide operatively linked to a promoter such that the open reading frame in the candidate polynucleotide is expressed. Methods of preparing cDNA and of constructing cDNA expression libraries are well known in the art, and any such methods can be used (see Sambrook et al., 1989; Perbal et al., 1988). Suitable plasmids can be constructed using standard recombinant DNA techniques or can be purchased from commercial suppliers.

In another embodiment of the invention, candidate polynucleotides encode variations of a known protease molecule. Polynucleotides encoding any known protease can be varied, including but not limited to members of the serine protease, aspartyl protease, cysteine protease, and metalloprotease families mentioned above. Preferably, amino acids involved in the recognition of the amino acid substrate of the known protease are varied.

Polynucleotides encoding proteases can be obtained, for example, from cells such as those mentioned above, or can be produced recombinantly or synthetically. The polynucleotides can then be mutated, either randomly or at specific sites, to produce polynucleotides encoding variations of known protease sequences which have altered substrate specificity. Site-specific mutagenesis is taught, for example, in Watkins et al., *Biotechniques* 15, 700–704 (1993), Weiner et al., *Gene* 126, 35–41 (1993), and Weiner et al., *Gene* 151,119–123 (1994). Optionally, polynucleotides encoding particular protease variations can be synthesized directly.

Preferably, candidate polynucleotides contain a selectable marker to facilitate subsequent selection of transfected target cells. Antibiotic resistance genes, such as a neomycin, puromycin, or phleomycin resistance gene, are particularly useful for this purpose.

Expression Cassettes According to the Invention

An "expression cassette" according to the invention is a polynucleotide construct which is capable of expressing a candidate polynucleotide molecule. Expression cassettes can be constructed using standard recombinant DNA techniques. Preferably, an expression cassette includes a candidate polynucleotide, a promoter, and a viral packaging signal. A variety of effective promoters, such as the CMV and β-actin promoters, are known in the art and can be operatively linked to the candidate polynucleotide molecules. Of course, the promoter must be selected to be operative in the particular target cell which is used in the method. The viral packaging signal must also be operative in the target cell. Selection of appropriate promoters and viral packaging signals is well within the skill in the art.

Other sequences can be included in an expression cassette. For example, primer sequences can be included, for use in amplifying the candidate polynucleotide molecules. Endoplasmic reticulum and/or Golgi retention/retrieval signals also can be included so that the encoded protease will be retained in the export pathway of the target cell (Nilsson & Warren, *Curr. Opin. Cell Biol.* 6(4), 517–21, 1994). If integration into the genome of the target cell is desired, expression cassettes can include sequences which permit such integration, such as viral long-terminal repeats (LTRs). Examples of LTRs include the LTR of the Rous sarcoma virus (Gorman et al., 1982, *Proc. Natl. Acad. Sci. U.S.A.* 79, 6777), the human cytomegalovirus LTR (Boshart et al., 1985, *Cell* 41, 521), and the Moloney MLV LTR (Van Beveren et al., 1980, *Proc. Natl. Acad. Sci. U.S.A.* 77(8), 3307–11).

Target Cells Useful in the Invention

"Target cells" should not express a level of the protease to be identified that would interfere with the inventive methods. Levels of protease activity can be determined using protease assays such as those described above to detect the cleavage of the particular protease recognition site to be used in the chimeric envelope protein. It is also possible to construct non-replicating viral display packages which comprise a reporter gene, such as β-galactosidase. In the presence of cells which express proteolytic activity, the inhibitory protein is cleaved from the chimeric envelope protein, the reporter gene is transferred to the target cell, and an increased amount of reporter gene product can be detected in the target cells. Cleavage of the inhibitory protein from the chimeric envelope protein can be visualized for example, on a Western blot following SDS-PAGE.

Target cells comprise polynucleotides which encode products and functions necessary for the formation of viral display packages, including packaging-defective Gag and Pol polypeptides, a chimeric envelope protein, as well as a retroviral packaging signal and viral long terminal repeats. Polynucleotides encoding these functions and products can be present on a single plasmid or on two or more plasmids. Any appropriate method can be used to transfect polynucleotides into target cells. Methods of transfecting polynucleotides into cells are well known and include, but are not limited to, DEAE- and calcium phosphate-mediated transfection, and electroporation. Variations of the calcium phosphate-mediated precipitation method appropriate for adherent cells, adherent cells released from the substratum with trypsin, and nonadherent cells are described in detail in Sambrook et al. (1989), at pages 16.32–16.40. Lipid compositions, such as Superfect by QIAGEN, can also be used for transfection as described above, either simultaneously with, before, or after introduction of the candidate polynucleotides.

If viral display packages which display a chimeric envelope protein are used, target cells should express on their surface a receptor for the substantially intact viral envelope protein used in the chimeric envelope protein. For example, if a Moloney murine leukemia virus envelope protein is used in the chimeric envelope protein, target cells should express the ecotropic CAT- 1 receptor (Kavanaugh et al., 1991, *Nature* 352, 729–31). Similarly, if the 4070A murine leukemia virus protein is used, target cells should express the amphotropic Pit-2/Ram-1 receptor (Miller et al., 1994, *Proc. Natl. Acad. Sci. U.S.A.* 91(1), 78–82). The receptors can be expressed naturally by the target cells, or polynucleotides encoding the receptors can be introduced into target cells, as described below.

If viral display packages which display a recombinant envelope protein are used, target cells should express on their surface a receptor for the envelope protein from which the recombinant envelope protein was derived. Thus, if the recombinant envelope protein is derived from a Moloney murine leukemia virus envelope protein, target cells should express CAT-1. If the recombinant envelope protein is derived from an influenza virus, target cells should express a sialic acid receptor for the influenza virus envelope protein (Higa et al., 1985, *Virology* 144, 279–82).

Some naturally-occurring proteases are expressed as zymogens—inactive forms of the protease that must be activated to express protease activity. Activation of the zymogen or "pro" form of a protease may occur, for example, through exposure to metal ions or through cleavage by a separate activating protease. When a protease is naturally expressed as a pro-form, the cDNA encoding the protease will encode the pro-form, rather than the active form. However, a number of proteases expressed in pro-form are activatable to a measurable extent by ubiquitous (e.g., furin-like) proteases present in target cells in addition to being activatable by cell-type specific proteases (Okumura et al., 1997, *FEBS Lett.* 402: 181–4; Sato et al., 1996, *FEBS Lett.* 393: 101–4; Pei & Weiss, 1995, *Nature* 375: 244–7). Further, target cells may be treated to activate the necessary proteolytic activity(ies) to allow activation of pro-form proteases in the methods of the invention. For example, growth factors, activating proteases or other protease-modulating compounds may be used to modulate protease activity in target cells (Campbell et al., 1994, *J Cell Physiol* 159: 1–10; Harano & Mizuno, 1994, *J. Biol Chem* 269: 20305–11).

In one embodiment, the target cells are viral packaging cells which produce viral display packages from packaging-defective viral genes. For example, viral packaging cells express defective gag, pol, and env genes. Suitable viral packaging cell lines include TELCeB.6, or any cell line that is negative for the protease in question and which comprises packaging defective gag andpol genes and a gene encoding a chimeric or recombinant envelope protein, and which can be transfected with packaging competent plasmids (e.g. cDNA expression plasmids). Other cells which can be used as target cells include, but are not limited to, members of established cell lines such as NIH 3T3 cells (ECACC no. 85111801), Colo 205 cells (ECACC no. 87061208), Jurkat E6.1 cells (ECACC no. 88042803), A431 cells (ATCC CRL1555), TE 671 cells (ATCC CRL8805), or HT 1080 (ATCC CCL121).

The above disclosure generally describes the present invention, and all references cited in this disclosure are incorporated by reference herein. A more complete understanding of the invention can be obtained by reference to the following specific examples which are provided for purposes of illustration only and are not intended to limit the scope of the invention.

EXAMPLE 1

This example demonstrates the utility of the invention for cloning of an unknown protease when the protease substrate sequence is known. For illustrative purposes, the cloning of the metalloproteinase, MT1-MMP, is described.

Amphotropic packaging cells are generated from MT1-MMP-negative TE671 cells; ATCC CRL-8805), by transfection with packaging-defective plasmids encoding retroviral gag and pol and chimeric env (see below). The packaging cell lines are then transfected with a cDNA expression library derived from RNA isolated from the fibrosarcoma cell line HT-1080 (ATCC Accession No. CCL-121) by superfection (QIAGEN). The cDNA expression library contains plasmids which contain cDNA molecules obtained from HT-1080 RNA under the control of a CMV promoter. The plasmids also contain the retroviral packaging signal, the retroviral long-terminal repeat, a neomycin resistance gene and primers for amplifying the cDNA molecules.

In addition to packaging-defective gag and pol genes, the TE671 cells contain an env gene which encodes a chimeric envelope protein. The chimeric envelope protein comprises, from N- to C-terminus (1) 146 amino acids of the C-terminal domain of CD40L (residues 116–261), (2) Pro-Leu-Gly*-Leu-Trp-Ala a cleavage site MT1-MMP, where * indicates the point of cleavage, and (3) a complete 4070A murine leukemia virus envelope protein.

After transfection with the cDNA library, the TE671 packaging cells are selected in neomycin for 2 weeks. 1/10 volume of the media from the TE671 packaging cells is then transferred to fresh TE671 packaging cells. This procedure is repeated until the cells have undergone at least 10 rounds of cell division, after which the majority of the TE671 packaging cells comprise an integrated cDNA sequence encoding a protease which recognizes the MMP protease recognition site. Genomic DNA is then extracted using a QIAAMP tissue kit (QIAGEN).

cDNA molecules which were integrated into the TE671 packaging cell genome are amplified by PCR, using primers complementary to sequences of the plasmids up- and downstream from the integrated cDNA molecules. The amplified DNA is then cleaved at the insertion sites for the cDNA molecules, and the sizes of the amplified products are determined on an agarose gel.

The major product on the agarose gel, containing a coding sequence for a protease which cleaved the MMP protease recognition site in the chimeric envelope protein, is sequenced using the dideoxynucleotide chain termination method (Sanger et al., *Proc. Natl. Acad. Sci. U.S.A.* 74, 5463, 1977). After sequencing, the predicted amino acid sequence of the identified protease is confirmed as that of MT1-MMP.

EXAMPLE 2

This example describes cloning of a gelatinase A (MMP-2)-related protease with an altered substrate specificity.

Point mutations are introduced into double-stranded MMP-2 cDNA molecules by incorporating into separate pools of the double-stranded DNA each of the four α-thiophosphate dNTPs (Shortle et al., *Proc. Natl. Acad. Sci. U.S.A.* 79, 1588, 1982; Shortle & Lin, *Genetics* 110, 539, 1985). The pools of mutated cDNA molecules are then combined and inserted into plasmids to form a cDNA expression library. The plasmids also contain a neomycin resistance gene, a retroviral packaging signal, and primers for amplifying the cDNA molecules. The plasmids are then transfected into cells which are negative for MMP-2 and unable to cleave the altered substrate sequence, e.g., NIH-3T3 cells, using calcium phosphate-mediated transfection (Sambrook et al., 1989).

In addition to packaging-defective gag and pol genes, the NIH-3T3 cells contain an env gene which encodes a chimeric envelope protein. The chimeric envelope protein comprises, from N- to C-terminus, (1) CD40L protein, (2) Pro-Gln-Ser-Ile-Ala-Gly-Gln, a recognition site for MMP-2 in which Ser has been substituted for Gly at the third position, and (3) a complete 4070A murine envelope protein. After transfection with the cDNA library, cells are grown to near-confluence. The cells are then transferred to a larger tissue culture vessel and exposed to neomycin, to select for cells which have become neomycin-resistant due to infection by a viral display package comprising a neomycin resistance gene.

The selected cells are grown to near confluence, and one-tenth of the culture medium (containing viral display packages) is transferred to another culture of NIH-3T3 packaging cells. This procedure is repeated 5–10 times. A QIAGEN genomic DNA amplification kit (QIAAMP tissue kit) is used to extract genomic DNA.

cDNA molecules which were integrated into the host cell genome are amplified by PCR, using primers complementary to sequences of the plasmids up- and downstream from the integrated cDNA molecules. The amplified DNA is then cleaved at the insertion sites for the cDNA molecules, and the sizes of the amplified products are determined on an agarose gel. The major product on the agarose gel, containing a coding sequence for a protease which cleaved the modified protease recognition site in the chimeric envelope protein, is sequenced using the dideoxynucleotide chain termination method (Sanger et al., 1977). After sequencing, the predicted amino acid sequence of the identified protease is determined.

What is claimed is:

1. A method of identifying a candidate polynucleotide molecule encoding a protease, comprising the steps of:
   incubating a first plurality of target cells which comprise candidate polynucleotides that are packaged into a viral display package wherein the viral display packages display chimeric envelope proteins which comprise (i) a substantially intact viral envelope protein which enhances fusion between a viral membrane and a target cell membrane, (ii) an inhibitory protein which impairs fusion between the substantially intact viral envelope protein and a target cell membrane, and (iii) a protease recognition site located between the substantially intact viral envelope protein and the inhibitory protein; and
   contacting the viral display packages produced by the first plurality of target cells with a second plurality of target cells, wherein infection of a member of the second plurality of target cells by a viral display package occurs only if a protease produced in a member of the first plurality of target cells removes the inhibitory protein from the chimeric envelope protein.

2. The method of claim 1 wherein members of the first and second pluralities of target cells are the same cell type.

3. The method of claim 1 wherein at least a third plurality of target cells is infected with a viral display package.

4. The method of claim 1 wherein said first plurality of target cells comprises a first plasmid comprising a candidate polynucleotide sequence and a retroviral packaging signal, and a viral long terminal repeat, and a second plasmid comprising a packaging defective polypeptide.

5. The method of claim 4 wherein the retroviral packaging signal, the viral long terminal repeat, and the polynucleotides which encode the packaging defective gag and pol polypeptides and the chimeric envelope protein are encoded in the same polynucleotide molecule as the candidate polynucleotide.

6. The method of claim 1 wherein the chimeric envelope protein comprises a substantially intact retroviral envelope protein.

7. The method of claim 6 wherein the substantially intact retroviral envelope protein is a murine leukemia virus envelope protein.

8. The method of claim 7 wherein the murine leukemia virus envelope protein is obtained from a murine leukemia virus selected from the group consisting of a 4070A virus and a Moloney murine leukemia virus.

9. The method of claim 1 wherein the inhibitory protein binds to a receptor present on the outer cell membrane of the target cell.

10. The method of claim 1 wherein the candidate polynucleotides are obtained from a cell which is likely to express a protease.

11. The method of claim 10 wherein the cell is a tumor cell.

12. The method of claim 10 wherein the cell is obtained from a tissue which is inflamed.

13. The method of claim 10 wherein the cell is obtained from a tissue which is undergoing remodeling.

14. The method of claim 10 wherein the cell comprises an infectious agent which expresses a protease.

15. The method of claim 10 wherein the cell is obtained from a tissue which is involved in wound healing.

16. The method of claim 1 wherein the candidate polynucleotide molecules are synthetic polynucleotides.

17. The method of claim 1 wherein the viral display package comprises a transferable label.

18. The method of claim 1 wherein the candidate polynucleotide molecule is integrated into a genome of a member of the second plurality of target cells.

19. The method of claim 18 wherein the candidate polynucleotide molecules further comprise a specific integration sequence.

20. The method of claim 19 wherein the specific integration sequence is a retroviral long terminal repeat.

21. The method of claim 1 wherein the candidate polynucleotide molecules comprise a coding sequence for an endoplasmic reticulum retention/retrieval signal.

22. The method of claim 1 wherein the candidate polynucleotide molecules comprise a coding sequence for a Golgi retention/retrieval signal.

23. The method of claim 1 wherein the candidate polynucleotide molecules comprise primers for amplifying the candidate polynucleotide molecules.

24. The method of claim 1, further comprising the step of amplifying the candidate polynucleotide molecule which encodes the protease.

25. The method of claim 24, further comprising the step of sequencing the amplified candidate polynucleotide molecule.

26. The method of claim 1 wherein the inhibitory protein is a CD40 ligand.

27. The method of claim 1 wherein the inhibitory protein is a leucine zipper polypeptide.

28. The method of claim 27 wherein the leucine zipper polypeptide is selected from the group consisting of GCN4, C/EBP, Fos, Jun, and c-myc.

29. The method of claim 1 wherein the inhibitory protein is selected from the group consisting of CD3 antigen, epidermal growth factor, stem cell factor, and insulin-like growth factor I.

30. The method of claim 1 wherein candidate polynucleotides are present in an expression cassette.

31. The method of claim 1 wherein candidate polynucleotides are obtained from a cell which is not known to express a protease.

32. The method of claim 1 wherein candidate polynucleotides are obtained from a cell which is known to express a protease.

33. The method of claim 1 wherein one or more of said pluralities of target cells subjected to a treatment to modulate protease activity.

34. The method of claim 34 wherein said treatment comprises contacting said cells with a protease-modulating compound, growth factor or protease.

35. A method of identifying a candidate polynucleotide molecule encoding a protease, comprising the steps of:

incubating a first plurality of target cells which comprise candidate polynucleotides that are packaged into a viral display package, wherein the viral packages display recombinant envelope proteins comprising a furin cleavage site located between a large glycoprotein subunit of the envelope protein and a transmembrane component of the envelope protein; and contacting the viral display packages produced by the first plurality of target cells with a second plurality of target cells, wherein infection of a member of the second plurality of target cells by a viral display package occurs only if a protease produced in a member of the first plurality of target cells activates the envelope protein by cleaving it at the furin cleavage site between the large glycoprotein subunit and the transmembrane component.

36. The method of claim 33 wherein the recombinant envelope protein is derived from a viral envelope protein selected from the group consisting of a Moloney murine leukemia virus envelope protein, a 4070A envelope protein, and an influenza virus envelope protein.

37. The method of claim 33 wherein members of the first and second pluralities of target cells are the same cell type.

38. The method of claim 35 wherein at least a third plurality of target cells is infected with a viral display package.

39. The method of claim 1 wherein the candidate polynucleotides are obtained from a cell which is likely to express a protease.

40. The method of claim 39 wherein the cell is a tumor cell.

41. The method of claim 39 wherein the cell is obtained from a tissue which is inflamed.

42. The method of claim 39 wherein the cell is obtained from a tissue which is undergoing remodeling.

43. The method of claim 39 wherein the cell comprises an infectious agent which expresses a protease.

44. The method of claim 39 wherein the cell is obtained from a tissue which is involved in wound healing.

45. The method of claim 35 wherein the candidate polynucleotide molecules are synthetic polynucleotides.

46. The method of claim 35 wherein the viral display package comprises a transferable label.

47. The method of claim 35 wherein the candidate polynucleotide molecule is integrated into a genome of a member of the second plurality of target cells.

48. The method of claim 45 wherein the candidate polynucleotide molecules further comprise a specific integration sequence.

49. The method of claim 46 wherein the specific integration sequence is a retroviral long terminal repeat.

50. The method of claim 35 wherein the candidate polynucleotide molecules comprise a coding sequence for an endoplasmic reticulum retention/retrieval signal.

51. The method of claim 35 wherein the candidate polynucleotide molecules comprise a coding sequence for a Golgi retention/retrieval signal.

52. The method of claim 35 wherein the candidate polynucleotide molecules comprise primers for amplifying the candidate polynucleotide molecules.

53. The method of claim 35, further comprising the step of amplifying the candidate polynucleotide molecule which encodes the protease.

54. The method of claim 51, further comprising the step of sequencing the amplified candidate polynucleotide molecule.

55. The method of claim 35 wherein candidate polynucleotides are obtained from a cell which is not known to express a protease.

56. The method of claim 35 wherein candidate polynucleotides are obtained from a cell which is known to express a protease.

57. The method of claim 4 wherein said packaging defective polypeptide is at least one of gag or pol.

58. The method of claim 4 wherein said second plasmid further comprises a chimeric envelope protein.

59. The method of claim 1 wherein said first plurality of target cells comprises a plasmid comprising a candidate polynucleotide sequence, a retroviral packaging signal, a viral long terminal repeat, polynucleotides which encode gag and pol polypeptides and a chimeric envelope protein.

60. The method of claim 6 wherein the substantially intact retroviral envelope protein is obtained from an influenza virus.

* * * * *